(12) United States Patent
Xue et al.

(10) Patent No.: US 6,920,350 B2
(45) Date of Patent: Jul. 19, 2005

(54) METHOD OF AND APPARATUS FOR DISPLAYING AND ANALYZING A PHYSIOLOGICAL SIGNAL

(75) Inventors: Joel Q. Xue, Germantown, WI (US); Shankara B. Reddy, Cedarburg, WI (US)

(73) Assignee: GE Medical Systems-Information Technologies, Inc., Milwaukee, WI (US)

( * ) Notice: Subject to any disclaimer, the term of this patent is extended or adjusted under 35 U.S.C. 154(b) by 396 days.

(21) Appl. No.: 09/922,627

(22) Filed: Aug. 6, 2001

(65) Prior Publication Data

US 2003/0028119 A1 Feb. 6, 2003

(51) Int. Cl.[7] .............................................. A61B 5/044
(52) U.S. Cl. ....................................................... 600/523
(58) Field of Search ................................ 600/523, 508, 600/509, 524, 525, 481, 485, 800

(56) References Cited

U.S. PATENT DOCUMENTS

| | | | |
|---|---|---|---|
| 4,898,181 A | | 2/1990 | Kessler |
| 4,974,598 A | * | 12/1990 | John ........................... 600/509 |
| 5,161,539 A | * | 11/1992 | Evans et al. ................. 600/508 |
| 5,365,936 A | * | 11/1994 | Kyu ............................ 600/523 |
| 5,474,078 A | * | 12/1995 | Hutson ....................... 600/512 |
| 5,640,966 A | * | 6/1997 | Heden et al. ............... 600/509 |
| 5,687,737 A | * | 11/1997 | Branham et al. ........... 600/523 |
| 5,782,773 A | * | 7/1998 | Kuo et al. ................... 600/523 |
| 5,803,084 A | * | 9/1998 | Olson .......................... 600/512 |
| 5,819,007 A | * | 10/1998 | Elghazzawi .................. 706/46 |
| 5,947,899 A | * | 9/1999 | Winslow et al. ............ 600/410 |
| 6,119,035 A | * | 9/2000 | Wang .......................... 600/509 |
| 6,424,853 B1 | * | 7/2002 | Tsukada et al. ............. 600/409 |
| 6,556,860 B1 | * | 4/2003 | Groenewegen ............. 600/509 |
| 2002/0029001 A1 | * | 3/2002 | Anderson et al. ........... 600/508 |
| 2002/0035333 A1 | * | 3/2002 | Meij et al. ................... 600/509 |
| 2002/0128565 A1 | * | 9/2002 | Rudy ........................... 600/509 |

FOREIGN PATENT DOCUMENTS

| | | | | |
|---|---|---|---|---|
| EP | 0383697 | | 8/1990 | |
| JP | 6-47022 | * | 2/1994 | ........... A61B/5/055 |
| JP | 6-63026 | * | 3/1994 | ........... A61B/5/402 |
| WO | WO 99/35558 | | 7/1999 | |

OTHER PUBLICATIONS

12–Lead Vectorcardiography; P.W. MacFarlane et al.; Butterworth–Heinemann Ltd., 1995; pp. 32–37.

"Mapping Techniques" by R.L. Lux; Comprehensive Electrocardiology, Theory and Practice in Health and Disease; editor P.W. MacFarlane et al.; Pergamon Press; vol. 2, pp. 1001–1013; Salt Lake City, Utah.

"Body–Surface Mapping" by L. De Ambroggi et al.; Comprehensive Electrocardiology, Theory and Practice in Health and Disease; editor P.W. MacFarlane et al.; Pergamon Press; pp. 1015–1030; Parma, Italy.

* cited by examiner

*Primary Examiner*—Jeffrey R. Jastrzab
(74) *Attorney, Agent, or Firm*—Andrus, Sceales, Starke & Sawall, LLP

(57) ABSTRACT

A method of displaying a representation of a physiological signal produced by a patient. The method includes the acts of obtaining a portion of at least one physiological signal acquired from the patient, determining an area to display, and constructing a virtual image representing at least a portion of the patient. The virtual image including (M) polygonal areas. The method further includes transforming the obtained signal to a plurality of values, assigning each value to one of the (M) polygonal areas, assigning a visual characteristic to each polygonal area based in part on the assigned values, and displaying at least a portion of the virtual image including the assigned visual characteristics. The invention further provides a method of optimal feature selection for the classification of the physiological signals produced by a patient.

44 Claims, 5 Drawing Sheets

FRONT

BACK $$V = \begin{bmatrix} V_{1,A} & V_{1,A+1} & \bullet & \bullet & \bullet & V_{1,B} \\ V_{2,A} & & & & & \\ \bullet & & & & & \\ \bullet & & & & & \\ \bullet & & & & & \\ V_{N,A} & & & & & V_{N,B} \end{bmatrix}$$

FIG. 3

$$V' = \begin{bmatrix} V'_{1,A} & V'_{1,A+1} & \bullet & \bullet & \bullet & V'_{1,B} \\ V'_{2,A} & & & & & \\ \bullet & & & & & \\ \bullet & & & & & \\ \bullet & & & & & \\ V'_{M,A} & & & & & V'_{M,B} \end{bmatrix}$$

FIG. 5

$$V'' = \begin{bmatrix} V''_1 \\ V''_2 \\ \bullet \\ \bullet \\ \bullet \\ V''_M \end{bmatrix}$$

FIG. 6

INTEGRATED PROCESSED MAP
| 1 | 13 | 25 | 37 | 49 | 61 | 73 | 85 | 97 | 109 | 121 | 133 | 145 | 157 | 169 | 181 |
|---|----|----|----|----|----|----|----|----|-----|-----|-----|-----|-----|-----|-----|
| 2 | 14 | 26 | 38 | 50 | 62 | 74 | 86 | 98 | 110 | 122 | 134 | 146 | 158 | 170 | 182 |
| 3 | 15 | 27 | 39 | 51 | 63 | 75 | 87 | 99 | 111 | 123 | 135 | 147 | 159 | 171 | 183 |
| 4 | 16 | 28 | 40 | 52 | 64 | 76 | 88 | 100 | 112 | 124 | 136 | 148 | 160 | 172 | 184 |
| 5 | 17 | 29 | 41 | 53 | 65 | 77 | 89 | 101 | 113 | 125 | 137 | 149 | 161 | 173 | 185 |
| 6 | 18 | 30 | 42 | 54 | 66 | 78 | 90 | 102 | 114 | 126 | 138 | 150 | 162 | 174 | 186 |
| 7 | 19 | 31 | 43 | 55 | 67 | 79 | 91 | 103 | 115 | 127 | 139 | 151 | 163 | 175 | 187 |
| 8 | 20 | 32 | 44 | 56 | 68 | 80 | 92 | 104 | 116 | 128 | 140 | 152 | 164 | 176 | 188 |
| 9 | 21 | 33 | 45 | 57 | 69 | 81 | 93 | 105 | 117 | 129 | 141 | 153 | 165 | 177 | 189 |
| 10 | 22 | 34 | 46 | 58 | 70 | 82 | 94 | 106 | 118 | 130 | 142 | 154 | 166 | 178 | 190 |
| 11 | 23 | 35 | 47 | 59 | 71 | 83 | 95 | 107 | 119 | 131 | 143 | 155 | 167 | 179 | 191 |
| 12 | 24 | 36 | 48 | 60 | 72 | 84 | 96 | 108 | 120 | 132 | 144 | 156 | 168 | 180 | 192 |
300
FIG. 7
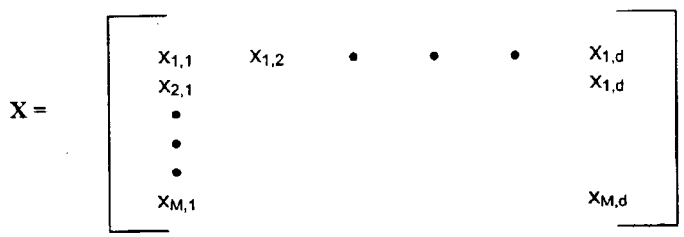
FIG. 8
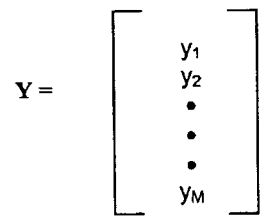
FIG. 9

METHOD OF AND APPARATUS FOR DISPLAYING AND ANALYZING A PHYSIOLOGICAL SIGNAL

BACKGROUND OF THE INVENTION

The invention relates to a method of and apparatus for displaying and analyzing a physiological signal of a patient, and particularly a method of and apparatus for displaying and analyzing a physiological signal where the physiological signal is represented by a signal acquired at the patient's body surface and the representative signal is transformed to include information not directly obtained from the patient.

It is known to acquire physiological signals with sensors attached at a patient's body surface. For example, an electrocardiograph senses electrical signals that are generated by a patient's heart with electrodes attached to the patient's chest and limbs. The electrodes produce one or more electrocardiogram (ECG) signals or leads. For example, ten electrodes may be attached to the patient to produce a twelve-lead ECG.

The electrocardiograph has a long history of being an important tool in diagnosing heart disease. While more and more new diagnostic tools are invented in cardiology (e.g., imaging technology), the electrocardiograph still remains an indispensable diagnostic tool. However, the presentation of the conventional twelve-lead ECG has remained relatively the same over the past half century.

SUMMARY OF THE INVENTION

A conventional twelve-lead ECG has limitations due to the limited information it contains. Accordingly, it would be beneficial to acquire a typical twelve-lead ECG (or similar representation of a physiological signal) and supplement the acquired multi-lead ECG with information from additional leads obtained using transformations that are derived from previously studied patients. With the acquired ECG and the supplemented information, a refined representation of the physiological signal may be generated. The refined representation may be used to provide a more detailed display of the physiological signal or to generate an optimal lead-set for further analysis.

In a first embodiment, the invention provides a method of displaying a representation of a physiological signal produced by a patient. The method includes the acts of obtaining a portion of at least one physiological signal acquired from the patient, determining an area to display, and constructing a virtual image representing at least a portion of the functional activity of the organ of interest. The virtual image including (M) polygonal areas. The method further includes transforming the obtained signal to a plurality of values, assigning each value to one of the (M) polygonal areas, assigning a visual characteristic to each polygonal area based in part on the assigned values, and displaying at least a portion of the virtual image including the assigned visual characteristics.

In a second embodiment, the invention provides a method of analyzing a physiological signal produced by a patient and generates an optimal set of signals for particular diagnosis. The method includes the acts of obtaining (N) voltages from a signal (e.g., a multi-lead ECG) representing the physiological signal, converting the (N) voltages to (M) values, where (M) is greater than (N), and optimizing the (M) values to (P) values, where (P) is less than (M).

BRIEF DESCRIPTION OF THE DRAWINGS

FIG. 3 is a matrix representing a plurality of sampled ECG leads.

FIG. 5 is a matrix representing a plurality of values at a plurality of sample points.

FIG. 6 is a vector having a plurality of integrated values.

FIG. 7 is an "Integrated Processed Map" having one hundred ninety-two cells.

FIG. 8 is a matrix including data relating to a plurality of previously studied patients.

FIG. 9 is a mean vector of the matrix in FIG. 8.

DETAILED DESCRIPTION

Before any embodiments of the invention are explained in full detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
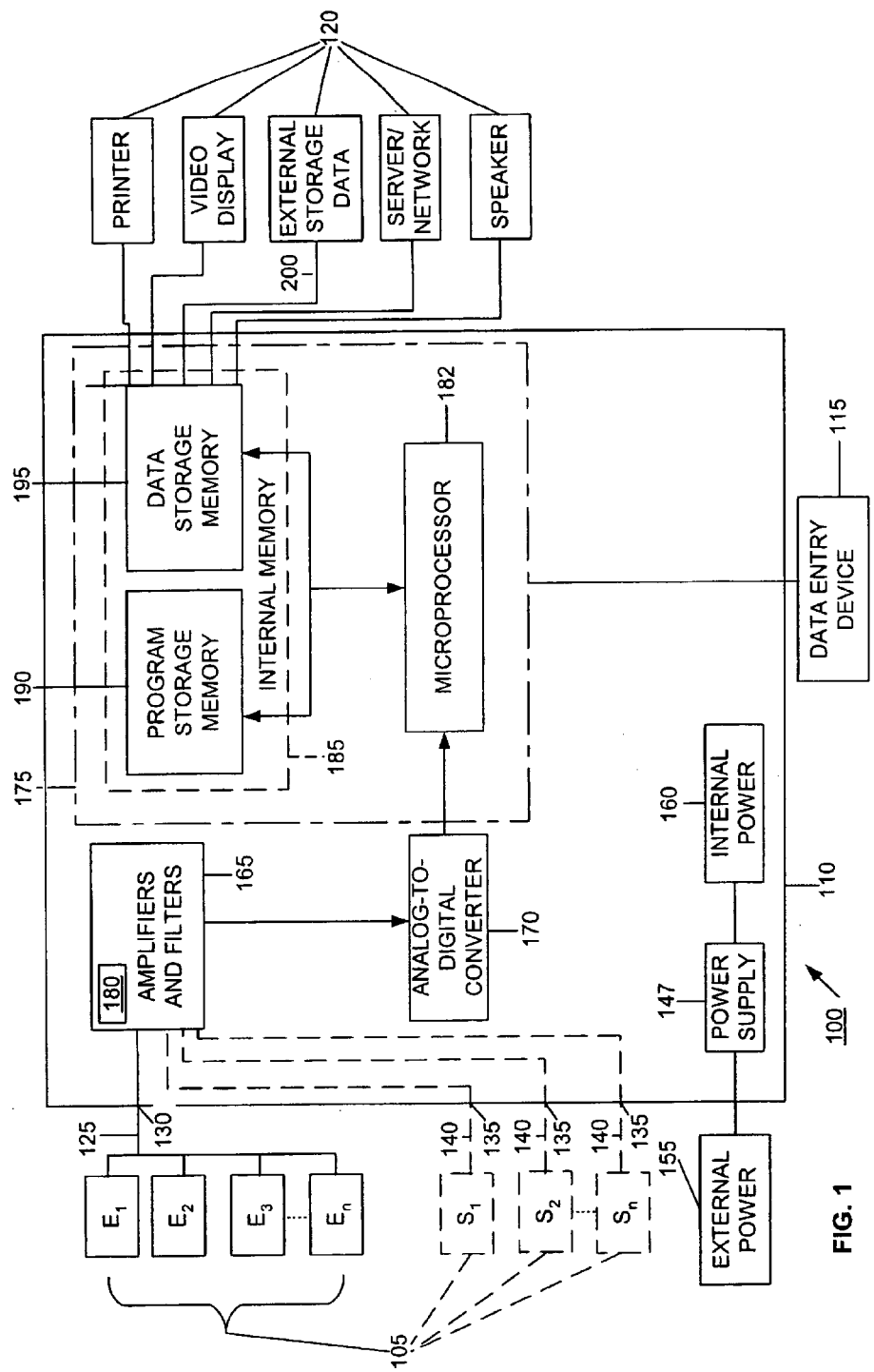
FIG. 1 is a schematic diagram of a physiological-signal-analysis device embodying the invention.

A physiological-signal-analysis device 100 embodying the invention is schematically shown in FIG. 1. In general terms, the physiological-signal-analysis device 100 includes one or more physiological-signal-input devices 105, a central unit 110, one or more operator-input devices 115, and one or more output devices 120. For example, the physiological-signal-analysis device 100 may be an electrocardiograph that acquires electrocardiogram (ECG) signals. It is envisioned that some aspects of the invention may apply for other physiological signals, especially electrical physiological signals (e.g., electromyography signals). For the purposes of simplifying the detailed description and unless specified otherwise, the physiological-signal-analysis device 100 is an electrocardiograph that acquires ECG signals.

The one or more physiological-signal-input devices 105 include a plurality of electrodes $E_1$, $E_2$ ... $E_n$ that are connectable to a patient. The electrodes $E_1$, $E_2$ ... $E_n$ sense electrical activity (e.g., ECG signals) generated by the patient. Specifically and for the electrocardiograph, the electrodes sense electrical signals that are generated by a patient's heart. The number of electrodes $E_1$, $E_2$ ... $E_n$ may vary. But for the embodiment shown, the number of electrodes is equal to ten and are connected to the patient in a standard twelve-lead ECG configuration.

The electrodes $E_1$, $E_2$ ... $E_n$ are connected to the central unit 110 by an interface cable 125. The interface cable 125 provides direct communication between the electrodes $E_1$, $E_2$ ... $E_n$ and an input terminal 130. The interface cable 125 allows for transmission of the sensed ECG signals from the patient to the central unit 110. The interface cable 125 is preferably a passive cable but, alternatively, the cable 125 may contain active circuitry for amplifying and combining the ECG signals into ECG leads (discussed further below). In other embodiments, the electrodes $E_1$, $E_2$ ... $E_n$ may be in communication with the central unit 110 through a telemetry-based transmitter that transmits radio frequency ("RF") signals to one or more antennas connected to the central unit 110.

For other physiological-analysis devices (e.g., a patient monitor), the one or more physiological-signal-input devices 105 may further include other physiological sensors $S_1$, $S_2 \ldots S_n$. The sensors $S_1, S_2 \ldots S_n$ are connectable to the patient and acquire physiological signals from the patient. For example, the sensors may include noninvasive blood pressure sensors, carbon dioxide sensors, pulse-oximetry sensors, temperature sensors, etc. Similar to electrodes $E_1$, $E_2 \ldots E_n$ and for the embodiment shown, the one or more sensors $S_1, S_2 \ldots S_n$ are connected to the central processing unit 110 at input terminals 135 by interface cables 140. In other embodiments, the one or more sensors $S_1, S_2 \ldots S_n$ may be in communication with the central processing unit via a telemetry transmitter as described above.

The operator-input device 115 allows an operator (e.g., a technician, nurse, doctor, etc.) to control the physiological-signal-analysis device 100 and/or to provide data to the central unit 110. The operator-input device 115 may be incorporated within the central unit 110 (e.g., one or more push buttons, one or more trim knobs, a pointing device, a keyboard etc.) or, alternatively, may be a stand-alone device (e.g., a stand-alone keyboard, etc.). Example operator-input devices 115 include a trim knob, a keyboard, a keypad, a touch screen, a pointing device (e.g., a mouse, a trackball), etc. Further and for some aspects of the invention, the one or more operator-input devices 115 may include data storage devices that include previously recorded physiological signals. Example data storage devices include magnetic-storage devices (e.g., a magnetic-disc drive), optical-storage devices (e.g., CD, DVD, etc.), and similar storage devices.

The central unit 110 includes a power supply 147. The power supply 147 powers the physiological-signal-analysis device 100 and receives input power either by an external power source 155 or an internal power source 160 (e.g., a battery, a solar cell, etc.). The central unit 110 also includes amplifying-and-filtering circuitry 165, analog-to-digital (A/D) conversion circuitry 170, and an analysis module 175. The amplifying-and-filtering circuitry 165, the A/D conversion circuitry 170, and the analysis module 175 may include discrete circuitry, integrated circuitry (e.g., an application-specific-integrated circuit), a processor and memory device combination, or combination of each type of circuit.

The amplifying-and-filtering circuitry 165 receives the physiological signals from the input terminals 130 and 135, and amplifies and filters (i.e., conditions) the physiological signals. For example, the amplifying-and-filtering circuitry 165 includes an instrumentation amplifier 180. The instrumentation amplifier 180 receives the ECG signals, amplifies the signals, and filters the signals to create a multi-lead ECG. The number of leads of the multi-lead ECG may vary without changing the scope of the invention. However, the preferred number of ECG leads is equal to twelve leads or sixteen leads.

The A/D conversion circuitry 170 is electrically connected to the instrumentation amplifier 180. The A/D conversion circuitry 170 receives the amplified and filtered physiological signals and converts the signals into digital physiological signals (e.g., a digital multi-lead ECG.) The digital physiological signals are then provided to the analysis module 175, which is coupled to the A/D conversion circuitry 170.

The analysis module 175 reads the digital physiological signals, analyzes the signals to create a developed signal, analyzes the developed signal to create a classification output, and displays the developed signals and/or the resulting classification output to the operator. In the embodiment shown, the analysis module 175 includes a microprocessor 182 and internal memory 185. The microprocessor 182 interprets and executes instructions stored as one or more software modules in internal memory 185. The memory 185 includes program storage memory 190 for storing the one or more software modules and data storage memory 195 for storing data. The implementation of the software including the one or more software modules is discussed in further detail below.

The output devices 120 may include a printer, a display, a storage device (e.g., a magnetic-disc drive, a read/write CD-ROM, etc.), a server or other processing unit connected via a network 200. Of course, other output devices may be added or attached (e.g., an audio-output device), and/or one or more output devices may be incorporated within the central unit 110. Additionally, not all of the outputs 120 are required for operation of the physiological-signal-analysis device 100.

In addition to the physiological-signal-analysis devices 100 described thus far, one skilled in the art will realize that some aspects of the invention may not require all elements described above. For example, the physiological signals may be previously recorded and supplied to the central unit via the operator-input device 115 or the network 200. For these embodiments, the physiological signals were previously recorded by other physiological-signal-analysis devices and are provided to the physiological-signal-analysis device 100 for analysis by the software modules described below. For a specific example, the physiological-signal-analysis device may be a standard personal computer including software modules that analyze obtained physiological signals previously stored on computer-readable media. Other devices are possible as is known in the art.

Having described the basic architecture of the physiological-signal-analysis device 100, different embodiments of operation are explained below. As was stated above, for simplifying the explanation of the detailed description and unless specified otherwise, the physiological-signal-analysis device 100 is an electrocardiograph that acquires a twelve-lead ECG.

In operation, an operator activates the electrocardiograph resulting in the software initializing the microprocessor 182 as is well known in the art. The operator then attaches the electrodes $E_1, E_2 \ldots E_n$ to the patient in a standard twelve-lead configuration and informs the electrocardiograph, via the data-entry device 115, to acquire the twelve-lead ECG signals. The electrocardiograph acquires and stores a segment of the multi-lead ECG as is known in the art. The stored multi-lead ECG includes a plurality of samples or data points for each lead, and the segment typically includes multiple cycles of the physiological signal. For example, the electrocardiograph typically records multiple cardiac cycles of the electrical signals that are generated by a patient's heart. However, for some aspects of the invention or for other physiological-signal-analysis devices 100, the segment may be a complete cardiac cycle, only a portion of the cardiac cycle, or may be only one sample of the cardiac cycle. For example, if the physiological-signal-analysis device is a patient monitor, then the acquired and stored multi-lead ECG signal may be a single sample used for displaying a representation of the physiological signal.

Once the electrocardiograph stores the multi-lead ECG signal representing the physiological signal, the electrocardiograph analyzes the multi-lead ECG signal to create a visual representation of at least a portion of the physiological signal and/or to create a classification of at least a portion of the physiological signal. For the description below and unless specified otherwise, the electrocardiograph will perform both analyses.

Displaying a Representation of a Physiological Signal

When analyzing the multi-lead ECG signal to create a visual representation of the physiological signal, the software obtains a portion of the raw or processed, such as a representative, cardiac cycle for analysis. The obtained portion may be for only one sample point or may be for multiple sample points of the multi-lead ECG. For example, the software may provide a visual representation of the ST-segment 250 (FIG. 2) of the cardiac cycle. However, the visual representation may be a representation of the Q-wave, R-wave, T-wave, etc., or a combination of multiple portions of the cardiac cycle (e.g., ST-segment and T-wave combination). In some embodiments, the operator may select the portion of the cardiac cycle to analyze. For the description below, the operator selects the ST-segment 250 for analysis. Upon selecting the ST-segment for analysis, the software analyzes ST-segment data from a particular instant of time. The operator may then request to analyze the ST-segment data from other time instants one at a time and "cycle" through the segments for observing the dynamic changes of ST segment distribution in the body surface map.

Figure 2:
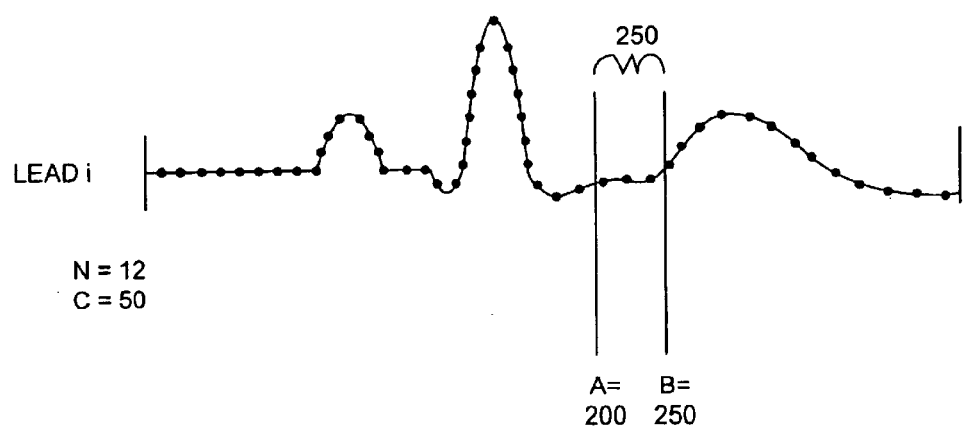
FIG. 2 is a representation of an electrical signal that is generated by a patient's heart.

As shown in FIG. 2, the letter (A) represents the beginning of the analyzed portion and the letter (B) represents the ending of the analyzed portion. The value of (B) is equal to (A+C), where (C) represents the number of samples in the portion of interest. For example, if the stored twelve-lead ECG for the complete cardiac cycle includes five hundred samples, then the portion of interest (e.g., the ST-segment) may be between (A=200) and (B=250), where (C=50). The voltages or data for all of the leads may be stored in a matrix (V) as is shown in FIG. 3. Each row of the table includes a lead having sampled voltages and each column is a sample point. Thus, any particular voltage is represented by ($v_{ij}$), where i=1 ... N and j=A ... B.

After a portion of the multi-lead ECG is obtained, the operator first selects a representation of the patient's exterior to display. For example, the operator may want to view the front body portion 255 (FIG. 4a), the back body portion 260 (FIG. 4b), or both the front and back body portions 255 and 260. Similarly, the operator may want to select a smaller region of the front and back portions 255 and 260. For the description below, it is assumed the operator selects both the front and back body portions 255 and 260. If a smaller area is selected, then, for some embodiments, the one or more acts discussed below are performed for the selected area only. For other embodiments, the software module does the analysis for the largest representative area (e.g. the front and back body portions 255 and 260), but only displays the selected area. In other embodiments, the software selects the area based on a default entry (e.g., no specified area is selected).

Figure 4A:
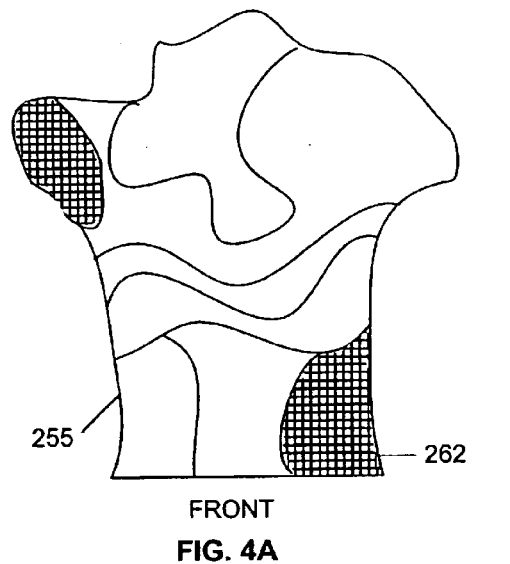
FIGS. 4A and 4B are schematic representations of front and back body portions, respectively, of a patient.
Figure 4B:
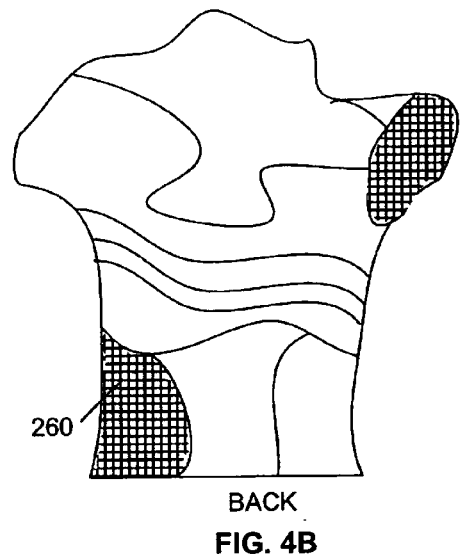

After determining an area to display, the software constructs a virtual image representing the selected portion of the patient's body surface. For the embodiment described, the virtual image is a three-dimensional (3D) surface area representing the front and back body portions 255 and 260 of the patient. When constructing the virtual image, the image is equally divided into (M) polygonal areas 262 (FIG. 4a). In the preferred embodiment, the value of (M) is equal to 192 (e.g., 81 for the front body portion 255, 81 for the back body portion 260), each polygonal area 262 is a four-sided rectangle, each polygonal area 262 has an equal amount of area, and all of the representative area is divided into the polygonal areas 262. However, for other embodiments, variations of the above requirements may be used. For example, the number of polygonal areas 262 may vary, the shape of each polygonal area 262 may vary, the size of the polygonal areas 262 may vary, etc.

The software then converts the voltages of each sample point (j) to a plurality of values. For example and for the twelve-lead ECG, the software takes the first sample of each lead (i.e., $V_{1,A} \ldots V_{N,A}$) and converts the (N) voltages to (M) values (i.e., $V'_{1,A} \ldots V'_{M,A}$), where (M) is greater than (N)). For the preferred embodiment, the conversion uses the technique described in Robert Lux, "Mapping techniques", in Comprehensive Electrocardiology, pp. 1001–1014, by P Macfarlane, Pergamon Press, 1989. Other conversion techniques may be used as is known in the art. By performing the conversion, the software uses information obtained from previously studied patients to supplement the acquired multi-lead signal. In other words, based on the previously studied patients, the software transforms the (N) multi-lead signal to a hypothetical (M) "multi-lead" signal. Of course, other techniques may be used and, depending on the technique used, the number of leads (N) and number of values (M) may vary. If the selected portion of the cardiac cycle includes multiple data points for each lead (e.g., the ST-segment is selected), then the software converts the (N) voltages of each sample to (M) values. The new (M) hypothetical leads may also be stored as a matrix (V') as is shown in FIG. 5. Each row of the table includes a "hypothetical" lead having (C) values and each column is a sample point. Thus, any particular value is represented by the letter ($v'_{i,j}$), where i=1 ... M and j=A ... B.

If the selected portion of the cardiac cycle includes multiple data points, then the software also calculates the integral for each hypothetical lead over the A-B segment. For example, the calculation of the integral may be made using the formula:

$$v''_i = \sum_{j=A}^{B} v'_{i,j}; i = 1 \ldots M.$$

Calculating the integral of each value point over the A-B segment reduces or condenses the columns down to just one column or vector (V") (FIG. 6) having (M) hypothetical lead values.

After reducing the (C) sample points to one vector (V"), the resulting column creates an "Integrated Potential Map" (IPM). As was explained above, the multi-dimensional surface area is divided into (M) polygonal areas. Each integrated value $v''_i$ is assigned or "mapped" to one of the polygonal areas. For the preferred embodiment, the resulting one hundred ninety-two integral values are assigned to the one hundred ninety-two polygonal areas using a one-to-one relationship. The assigning of the values to a polygonal area results in the IPM having (M) cells. For the specific embodiment described, an IPM 300 (FIG. 7) is created having 192 cells where each cell includes a value $v''_i$. The cells 1–48 and 145–192 are values corresponding to the back of the patient and cells 49–144 correspond to the front of the patient.

After assigning the values, a visual characteristic is assigned to each polygonal area. As used herein, the visual characteristic is a distinguishing visual attribute for each area. For example, depending on the value of the area, a color is assigned to the area. In other words, if a value is within a first range, then green may be assigned to that area.

Further, if a value is within a second range, then red may be assigned to that area. A pseudo color-coding scheme is employed. Similarly, other characters or symbols may be used in place of the colors and other algorithms may be used for determining the visual characteristic. Of course, if a selected portion of the display is requested, then the visual characteristics may be assigned only to the request portion.

After assigning the visual characteristics, the software displays the selected portion of the multidimensional area. The display may be via a visual display device such as a monitor, or a hard-copy printer. Alternatively, the outcome may be stored in a memory device and recalled later by the electrocardiograph or by another device 100. Further, the software may highlight the original location of the electrodes, or highlight the location of the original (N) leads.

When viewing the display, the operator may determine whether the display is typical or normal, or whether the display is atypical (e.g., the patient has acute cardiac ischemia or myocardial infarction). An example software tool that may be used to help generate the display is an OpenGL brand software package sold included in most operating systems.

Although, the above description was over a portion of the cardiac cycle having multiple samples, a body potential map may be created for just one sample. The software performs the same steps as above except, since only one row of samples is transformed, the software does not perform the integration to create a vector (V").

Classifying a Physiological Signal

In addition to displaying a representation of the physiological signal, the physiological-signal-analysis device 100 may also analyze and classify the physiological signal. In some embodiments of the invention, not all of the above-identified acts are performed. Further, in other embodiments of the invention, the physiological-signal-analysis device 100 only performs the function of displaying the representation. Preferably, the physiological-signal-analysis device 100 performs both the above acts and classifies the physiological signal.

As was discussed above, the portion of interest used for this description is the ST-segment 250. However it is envisioned that the analysis may be extended to other components or portions of the cardiac cycle. For example, the Q-wave, R-wave, ST-segment, T-wave, or a combination of the different components (e.g., ST-segment and T-wave combination) may be analyzed. When analyzing the combination of different components, each component is analyzed separately, and then the resulting separate analyses are analyzed together. In addition, the software may combine the separately analyzed portions to analyze the complete or whole cardiac cycle. Further, the software may separately analyze multiple cardiac cycles and average the resulting analyzed cycles.

With the IPM 300, the software reduces the (M) hypothetical leads to (P) optimal values or leads for a particular diagnosis, for example, acute cardiac ischemia. Reducing the number of values from (M) to (P) provides better analysis over the original lead-set. In other words, the original (N) leads are expanded to (M) hypothetical lead values based on prior obtained patient information, and then reduced to (P) optional lead values containing the optimal amount of information. The (P) optional lead values may then be applied to pattern recognition modules to classify the portion of interest. By optimizing the IPM 300, a hypothetical or optimal lead set is created providing more information from the hypothetical lead set than the original lead set. In the preferred embodiment, the software reduces the one hundred ninety-two integral amplitude values down to twelve optimal lead values. However, the number of optimal values may vary.

For the preferred embodiment, the software uses principal component analysis (PCA) to condense the (M) hypothetical lead values to the (P) optimal lead values based on a previously created database of patients. The purpose of PCA is to remove redundant information and obtain the optimal feature set for classification or further analysis.

The software obtains from memory, a previous stored database having a substantial number of entries (e.g., six thousand patients). The letter (D) represents the number of patients. The entries include (M) values of previously studied patients having various conditions. For example, if the ST-segment is the portion of interest then the database may include two thousand samples of patients diagnosed with acute myocardial infarction, two thousand patients diagnosed with unstable angina, and two thousand patients diagnosed as being normal. The data is stored as a matrix (X) (FIG. 8), which is a (M) by (D) matrix. In other words, each column represents a patient having an IPM. The value of (D) is only limited to the amount of memory available, and other types of patients with different conditions or information may be used.

After obtaining the stored matrix, the software computes a covariance matrix ($C_x$) with the formula $$C_x = (X - Y_x)(X - Y_x)^T$$

where (X) is matrix 305, (Y) is the mean vector of X, and $(X-Y)^T$ is the transpose of (X-Y). The mean vector Y is represented in FIG. 9 and each value $y_i$ is calculated using the formula:

$$y_i = \frac{1}{D} \sum_{j=1}^{D} x_{i,j}, \; i = 1 \ldots M$$

The covariance matrix ($C_X$) has a size (M) by (M) (e.g., one hundred ninety-two by one hundred ninety-two).

After calculating the covariance matrix ($C_X$), the software applies PCA analysis to the covariance matrix ($C_X$) with the formula $$C_X = USV^T,$$

where (U) and (V) are orthogonal matrices, S is a diagonal matrix (also referred to as principal components). The diagonal elements of the diagonal matrix are arranged in descending order. The matrices (U), (S) and (V) each have a size (M) by (M). The matrices (U) and (V) are each orthogonal; that is, their columns are orthogonal, i.e., $$\sum_{i=1}^{M} U_{i,k} U_{i,n} = \delta_{kn} \; 1 \leq k \leq M, 1 \leq n \leq M$$

$$\sum_{j=1}^{M} V_{j,k} V_{j,n} = \delta_{kn} \; 1 \leq k \leq M, 1 \leq n \leq M$$

For the embodiment described, the first twelve elements represent more than 98% of the signals energy, i.e.

$$\frac{\sum_{i=1}^{12} s_i}{\sum_{j=1}^{192} s_j} * 100 > 98.$$

By retaining the first twelve principal components, a majority of the information is kept.

The software uses the first (P) columns (e.g., P=12) of matrix (U) as ($U_1$), uses the first (P) by (P) submatrix from the upper corner of (S) as ($S_1$), and uses the first (P) columns from (V) as ($V_1$). The approximation matrix, $\tilde{C}_X$, may then be formed as follows:

$$\tilde{C}_X = U_1 S_1 V_1^T$$

After calculating the submatrix ($\tilde{C}_X$), the software calculates the optimized values or leads. $U_1$ is used for representing projection matrix. That is, the vector $Y_{(M)input}$ (e.g., vector V") is reduced or condensed to a new (P) lead vector with the equation:

$$Y_{(P)new} = U_1^T Y_M$$

where $Y_{(P)new}$ is the new (P) optimal lead set based on PCA reduction and the input lead set. For the embodiment shown, $Y_{(M)input}$ is vector V" (FIG. 6). However, for other embodiments, other input lead sets may be used.

With the new optimal set, the software can classify the segment. For example, the software may locate the ST elevation and maximum ST depression for the new optimal lead set.

Figure 10:
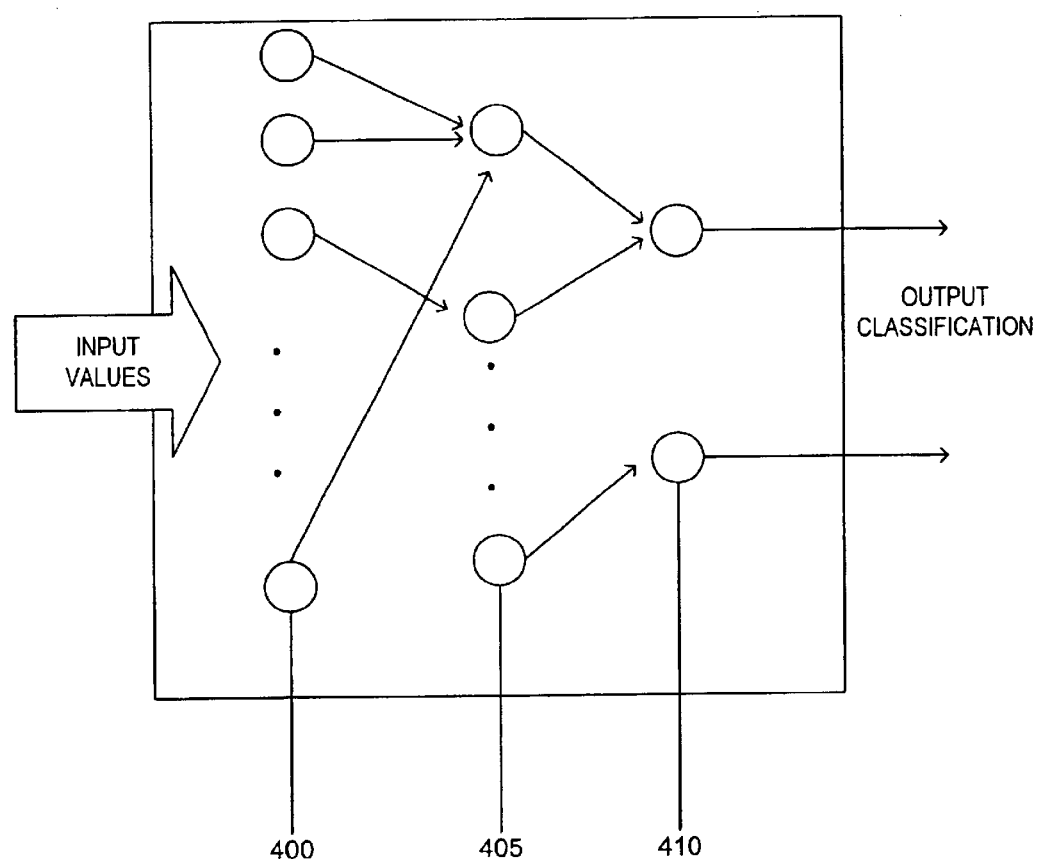
FIG. 10 is a schematic diagram of a neural network model.

The optimal lead set may also be used for further interpretation. An interpretation/pattern recognition method may be used to differentiate optimal lead sets into normal and abnormal categories. Pattern recognition models may include neural networks, fuzzy logic, or other statistical models like a Bayesian classifier. An example of a neural network model is shown in the following FIG. 10, where the model has 3 layers: input layer 400, hidden layer 405 and output layer 410. The input layer receives the (P) values for the optimal lead set, the hidden layer applies nonlinear mapping for the optimal lead set, and the output layer generates prediction results based on the nonlinear mapping. Other pattern recognition models may be used as is known in the art.

As can be seen from the above, the invention provides a new and useful physiological-signal-analysis device for displaying and analyzing a physiological signal of a patient. The invention also provides a new and useful method of displaying and analyzing a physiological signal of a patient, and a new and useful software tool for displaying and analyzing a physiological signal. Various features and advantages of the invention are set forth in the following claims.

What is claimed is:

1. A method of displaying a representation of a physiological signal produced by an organ of interest of the patient, the method comprising the acts of:
    obtaining a portion of at least one physiological signal, the obtaining act including acquiring the at least one physiological signal from the exterior of the patient;
    determining a surface area of the exterior of the patient to display, wherein the surface area of the patient is different from the organ of interest;
    constructing a three-dimensional virtual image of the surface area of the patient to be displayed and dividing the representative surface area into (M) polygonal areas;
    transforming the obtained signal to a plurality of values;
    assigning each value to one of the (M) polygonal areas;
    assigning a visual characteristic to each polygonal area based in part on the assigned values; and
    displaying at least a portion of the virtual image including the assigned visual characteristics.

2. A method as set forth in claim 1 wherein the act of obtaining a portion of at least one physiological signal includes the acts of placing a plurality of electrodes on the exterior of the patient and obtaining at least a portion of the multi-lead electrical signal acquired from the plurality of electrodes.

3. A method as set forth in claim 1 wherein the act of obtaining a portion of at least one physiological signal includes the act of obtaining at least a portion of a multi-lead electrocardiogram (ECG) acquired from the patient's exterior.

4. A method as set forth in claim 3 wherein the multi-lead ECG is a twelve lead ECG.

5. A method as set forth in claim 4 wherein the obtained portion of the representative signal includes one data point for each lead.

6. A method as set forth in claim 4 wherein the obtained portion of the multi-lead ECG includes a plurality of data points representing a portion of the cardiac cycle.

7. A method as set forth in claim 6 wherein the obtained portion of multi-lead ECG includes the ST-wave of the cardiac cycle.

8. A method as set forth in claim 1 wherein the act of obtaining at least a portion of the at least one physiological signal includes the acts of attaching a sensor to the exterior of the patient and sensing the physiological signal with the sensor to obtain the at least one physiological signal.

9. A method as set forth in claim 8 wherein the sensor includes a plurality of electrodes.

10. A method of displaying a representation of a physiological signal produced by an organ of interest of the patient, the method comprising the acts of:
    obtaining a portion of at least one physiological signal acquired from the exterior of the patient, including the act of reading the at least one physiological signal from a memory device;
    determining a surface area of the exterior of the patient to display, wherein the surface area of the patient is different from the organ of interest;
    constructing a three-dimensional virtual image of the surface area of the patient to be displayed and dividing the representative surface area into (M) polygonal areas;
    transforming the obtained signal to a plurality of values;
    assigning each value to one of the (M) polygonal areas;
    assigning a visual characteristic to each polygonal area based in part on the assigned values; and
    displaying at least a portion of the virtual image including the assigned visual characteristics.

11. A method as set forth in claim 1 wherein the virtual image represents at least a portion of the body surface of the patient.

12. A method as set forth in claim 1 wherein each polygonal area has a size and a shape, and wherein the sizes and shapes are equivalent areas.

13. A method as set forth in claim 1 wherein each polygonal area is a four-sided polygon.

14. A method as set forth in claim 1 wherein the act of assigning a visual characteristic to each polygonal area includes assigning a color to each polygonal area, based at least in part on the corresponding assigned value.

15. A method as set forth in claim 1 wherein the act of assigning a visual characteristic to each polygonal area includes assigning a character to each polygonal area, based at least in part on the corresponding assigned value.

16. A method of displaying a representation of a physiological signal produced by an organ of interest of a patient, the method comprising the acts of:
obtaining a portion of at least one physiological signal, the obtaining act including acquiring the at least one physiological signal from a twelve lead electrocardiogram (ECG) acquired from the exterior of the patient, wherein the physiological signal includes one data point for each lead of the ECG;
determining an area to display;
constructing a virtual image including (M) polygonal areas;
transforming the data points of the twelve leads of the ECG to (M) values;
assigning each of the (M) value to one of the (M) polygonal areas such that each polygonal area has one of the (M) values;
assigning a visual characteristic to each polygonal area based in part on the assigned values; and
displaying at least a portion of the virtual image including the assigned visual characteristics.

17. A method as set forth in claim 1 wherein (M) is equal to one hundred ninety-two.

18. A method of displaying a representation of an electrocardiogram (ECG), the method comprising the acts of:
obtaining at least a portion of a multi-lead ECG acquired from the patient's exterior wherein the obtained portion of the ECG includes a plurality of data points for each lead representing a portion of the cardiac cycle;
determining an area to display;
constructing a virtual image including (M) polygonal areas;
transforming the obtain portion of the multi-lead ECG to (M) values;
assigning each value to one of the (M) polygonal areas, the assigning act resulting in each polygonal area having one of the (M) values;
assigning a visual characteristic to each polygonal area based in part on the assigned values; and
displaying at least a portion of the virtual image including the assigned visual characteristics.

19. A method as set forth in claim 18 wherein the number of obtained leads is twelve leads.

20. A method as set forth in claim 19 wherein (M) is equal to one hundred ninety-two.

21. A method as set forth in claim 18 wherein the act of obtaining at least a portion of a multi-lead ECG includes the acts of attaching a sensor to the patient's exterior, sensing the ECG with the sensor, and creating the multi-lead ECG.

22. A method as set forth in claim 21 wherein the sensor includes a plurality of electrodes.

23. A method as set forth in claim 18 wherein the act of obtaining at least a portion of a multi-lead ECG includes the acts of reading at least a portion of the multi-lead ECG from a memory device.

24. A method as set forth in claim 18 wherein the virtual image is a three-dimensional surface area representing at least a portion of the patient.

25. A method as set forth in claim 18 wherein the (M) polygonal areas are regions on the three-dimensional surface area, wherein the (M) polygonal areas do not overlap, and wherein each polygonal area includes the same amount of area.

26. A method as set forth in claim 25 wherein each polygonal area is a four-sided polygon.

27. A method as set forth in claim 18 wherein the act of constructing a virtual image includes the acts of determining the portion of the patient to be represented, creating a multidimensional surface area representing the portion of the patient, determining the value of (M), and dividing the representative surface area into (M) polygonal areas.

28. A method as set forth claim 18 wherein the act of assigning a visual characteristic to each polygonal area includes assigning a color to each polygonal area based at least in part on the corresponding assigned value.

29. A method of analyzing a physiological signal produced by a patient and generating an optimal set of signals for particular diagnosis, the method comprising the acts of:
obtaining (N) voltages from (N) signals, respectively, the (N) signals representing the physiological sign, (N) being greater than one;
converting the (N) voltages to (M) values, where (M) is greater than (N);
repeating the act of obtaining (N) voltages (C) times, the repeating act resulting in (C) sets of (N) voltages;
repeating the act of converting the (N) voltages to (M) values for each set of (N) voltages, the repeating act resulting in (C) sets of (M) values; and
condensing the (C) sets of (M) values to one set of (M) values;
optimizing the one set of (M) values to (P) values, where (P) is less than (M).

30. A method as set forth in claim 29 and further comprising classifying the physiological signal with the (P) optimized values.

31. A method as set forth in claim 30 wherein the act of classifying the physiological signal includes the act of applying the (P) optimized values to a pattern recognition model for obtaining a classification output.

32. A method as set forth in claim 30 wherein the act of classifying the physiological signal includes the act of applying the (P) optimized values to a neural network for obtaining a classification output.

33. A method as set forth in claim 30 wherein the act of classifying the physiological signal includes the act of applying the (P) optimized values to a fuzzy algorithm for obtaining a classification output.

34. A method as set forth in claim 30 wherein the act of classifying the physiological signal includes the act of applying the (P) optimized values to a Bayesian decision logic for obtaining a classification output.

35. A method as set forth in claim 29 wherein (N) signals representing the physiological signal form a (N) multi-lead electrocardiogram.

36. A method as set forth in claim 35 wherein (N) is equal to twelve, (M) is equal to one hundred ninety-two, and (P) is equal to twelve.

37. A method as set forth in claim 29 wherein the physiological signal includes electrical signals that are generated by the patient's heart in a cardiac cycle, and wherein the (C) sets of (N) voltages are an (N) multi-lead representation of a portion of the cardiac cycle.

38. A method as set forth in claim 29 wherein the act of obtaining the (N) voltages includes the acts of attaching a sensor to the patient's exterior, sensing the physiological signal with the sensor to obtain (N) analog physiological signals, and sampling each signal to produce the (N) voltages.

39. A method as set forth in claim 38 wherein the sensor includes a plurality of electrodes.

40. A method as set forth in claim 29 wherein the act of obtaining (N) voltages includes the act of reading the (N) voltages from a memory device.

41. A method as set forth in claim 29 wherein the (C) sets of (M) values result in (M) virtual signals having (C) data points, and wherein the act of condensing the (C) sets of (M) values includes the act of integrating the (M) values over the (C) data points.

42. A method as set forth in claim 29 wherein the act of optimizing the (M) values to (P) values includes the acts of obtaining a database of previously recorded comparison values, computing a covariance matrix, and applying principal component analysis to the covariance matrix.

43. A method as set forth in claim 29 wherein the act of obtaining (N) voltages includes concurrently obtaining the (N) voltages from (N) signals, respectively.

44. A method as set forth in claim 29 wherein (N) is equal to twelve, (M) is equal to one hundred ninety-two, and (P) is equal to twelve.

* * * * *